US012409333B2

(12) United States Patent
Smits et al.

(10) Patent No.: US 12,409,333 B2
(45) Date of Patent: Sep. 9, 2025

(54) TREATMENT PAD FOR A DIELECTRIC BARRIER DISCHARGE PLASMA TREATMENT

(71) Applicant: PlasmaCure B.V., Nijmegen (NL)

(72) Inventors: Paulien Smits, Eindhoven (NL); Sofie Baselmans, Eindhoven (NL); Elisabeth Frieda De Ridder, 's-Gravenhage (NL); Jeroen Antoine Jozef Mulder, Weert (NL); Wouter Bastiaan Zeper, Eindhoven (NL)

(73) Assignee: PlasmaCure B.V., Nijmegen (NL)

( * ) Notice: Subject to any disclaimer, the term of this patent is extended or adjusted under 35 U.S.C. 154(b) by 343 days.

(21) Appl. No.: 18/267,760

(22) PCT Filed: Dec. 17, 2021

(86) PCT No.: PCT/NL2021/050775
§ 371 (c)(1),
(2) Date: Jun. 15, 2023

(87) PCT Pub. No.: WO2022/131921
PCT Pub. Date: Jun. 23, 2022

(65) Prior Publication Data
US 2024/0042225 A1 Feb. 8, 2024

(30) Foreign Application Priority Data

Dec. 17, 2020 (NL) .................................... 2027148

(51) Int. Cl.
*A61N 1/44* (2006.01)
*A61B 18/04* (2006.01)
(52) U.S. Cl.
CPC .............. *A61N 1/44* (2013.01); *A61B 18/042* (2013.01)

(58) Field of Classification Search
CPC ................... A61N 1/44; A61B 18/042; A61B 2018/00583
(Continued)

(56) References Cited

U.S. PATENT DOCUMENTS

2010/0175987 A1 * 7/2010 Creyghton ........... H05H 1/2441
422/186.29
2012/0259270 A1 10/2012 Wandke et al.
(Continued)

FOREIGN PATENT DOCUMENTS

WO WO 2012/106735 A2 8/2012
WO WO 2019/066113 A1 4/2019
WO WO 2019/125149 A1 6/2019

OTHER PUBLICATIONS

European Patent Office, International Search Report in corresponding International Application No. PCT/NL2021/050775, dated Apr. 13, 2022 (4 pages).

*Primary Examiner* — Linda C Dvorak
(74) *Attorney, Agent, or Firm* — Leydig, Voit & Mayer, Ltd.

(57) ABSTRACT

A treatment pad for a dielectric barrier discharge plasma treatment of a tissue to be treated of an electrically conducting body, which tissue is used as a counter electrode, said treatment pad comprising: a treatment zone, arranged for at least covering the tissue to be treated; a pattern of one or more active areas, integrated in the treatment zone and arranged for generating a dielectric barrier discharge plasma, each said one or more active areas comprising: a first electrode to be coupled to a high voltage power source; a dielectric formed by a coating or foil of a flexible material so that the dielectric shields the first electrode from the tissue to be treated; and a spacer comprising a structured surface of protrusions adjacent a side of the dielectric facing the tissue to be treated; wherein the treatment zone comprises a (Continued)

complementary pattern of non-active areas, such that a complementary part of the tissue to be treated is covered by the said one or more active areas when the treatment pad is reapplied on the object with an offset.

17 Claims, 9 Drawing Sheets

(58) Field of Classification Search
USPC .......................................................... 606/32
See application file for complete search history.

(56) References Cited

U.S. PATENT DOCUMENTS

| | | |
|---|---|---|
| 2015/0157870 A1 | 6/2015 | Kalghatgi et al. |
| 2017/0136252 A1 | 5/2017 | Weltmann et al. |
| 2018/0140824 A1 | 5/2018 | Pemen et al. |
| 2019/0223280 A1 | 7/2019 | Wandke et al. |
| 2019/0327823 A1 | 10/2019 | Hahnl et al. |
| 2020/0069956 A1 | 3/2020 | de Penning et al. |

* cited by examiner

TREATMENT PAD FOR A DIELECTRIC BARRIER DISCHARGE PLASMA TREATMENT

CROSS-REFERENCE TO RELATED APPLICATIONS

This patent application is a U.S. National Phase of PCT International Application No. PCT/NL2021/050775, filed Dec. 17, 2021, which claims priority to The Netherlands Application No. 2027148, filed Dec. 17, 2020, which are both expressly incorporated by reference in their entireties, including any references contained therein.

FIELD OF THE INVENTION

The invention relates to devices for generating non-thermal plasma, in particular, that can be applied for treatment of living tissue.

BACKGROUND OF THE INVENTION

Cold plasmas have considerable potential for skin conditioning, disinfection of skin and wound healing. From U.S. Pat. No. 9,005,188, EP2670477 and EP3297724 dielectric barrier discharge plasma treatment pads are known, having flexible electrodes to be able to treat an irregularly shaped tissue with plasma. However, these treatment pads are likely only suitable for treating relatively small wounds.

To treat a larger wound, use of several distinct pads can be impractical because of difficulties with proper attachment of the pad to the wound and the risk that parts of the wound will be overtreated or not treated at all.

Simply increasing the pad size may also lead to difficulties because a larger electrode causes more capacitive loading. This results in a lower voltage, which can lead to failure to ignite the plasma and/or inhomogeneous plasma.

To obviate this, one may use a different power source. However, this would introduce new challenges to maintain compliance with electrical safety requirements. For example, the dielectric barrier in the pad and the high voltage cables may need a higher breakdown voltage, or PCB traces in the power source may need to be spaced further apart.

Such changes could increase cost price of the pad quite significantly or make the material much less flexible, hence unusable for its purpose. Thus, some of these changes are challenging and it may not be possible to establish compliance with the electrical safety requirements for the entire system.

The present invention focuses on a cold plasma device which can treat a larger tissue surface, without the drawbacks described.

SUMMARY OF THE INVENTION

In summary, embodiments of the invention pertain to a treatment pad for a dielectric barrier discharge plasma treatment of a tissue surface to be treated of an electrically conducting body, which tissue is used as a counter electrode. The treatment pad comprises a treatment zone, arranged for at least covering the tissue to be treated, with a pattern of one or more active areas integrated in the treatment zone and arranged for generating a dielectric barrier discharge plasma.

Each of the one or more active areas comprises a first electrode to be coupled to a high voltage power source, a dielectric formed by a coating or foil of a flexible material so that the dielectric shields the first electrode from the tissue to be treated, and a spacer comprising a structured surface of protrusions adjacent a side of the dielectric facing the surface to be treated.

The treatment zone comprises a complementary pattern of non-active areas, such that a complementary part of the tissue to be treated is covered by the said one or more active areas when the treatment pad is reapplied on the object with an offset.

For example, the treatment pad may be applied on the tissue surface to be treated, with the treatment zone covering the entire tissue surface to be treated. The treatment zone comprises a pattern of one or more active areas, e.g. arranged for providing plasma treatment to a first part of the surface to be treated. The treatment zone further comprises a complementary pattern of one or more non-active areas, e.g. arranged for covering, yet not providing any treatment to, a second part of the tissue surface to be treated. The complementary pattern of non-active areas is complementary to the pattern of active areas in that, combined, the pattern of non-active areas and the pattern of active areas may fill out or complete the treatment zone. Moreover, the pattern of active areas and the complementary pattern of non-active areas are complementary in that they are transposable relative to the surface to be treated by reapplying the treatment pad with an offset, without the risk of undertreatment or overtreatment of the surface to be treated, by minimizing the overlap between patterns of active areas after reapplying the treatment pad. The treatment zone may be bounded by an inactive border portion forming an edge of the treatment pad.

For example, by reapplying the treatment pad with an offset, e.g. rotating the treatment pad by 180 degrees in plane of the treatment zone, the treatment zone can again be arranged for covering the entire surface to be treated, yet with a different relative orientation. Now, the pattern of active areas may cover the second part of the surface to be treated, and the complementary pattern of non-active areas may cover the first part of the surface to be treated. As a result, the entire surface to be treated can be covered and treated by the pattern of active areas in multiple stages, e.g. two or more stages, which allows the use of relatively small active areas within a relatively large treatment zone, to treat a large surface to be treated.

By having a treatment pad with a treatment zone that comprises a complementary pattern of non-active areas, such that a complementary part of the surface to be treated is covered by the one or more active areas when the treatment pad is reapplied on the object with an offset, the treatment pad can provide dielectric barrier discharge plasma treatment to relatively large surfaces, without the risk that parts of the surface are undertreated or overtreated and without the effects of capacitive loading.

Surprisingly, the present invention has found a solution that does not require changes to the flexible electrode design and does not require a different electrode design. The innovative concept makes use of active areas in a non-obvious way, by using a pattern of one or more active areas and a complementary pattern of non-active areas to treat a complementary part of the surface to be treated by reapplying the pad with an offset.

BRIEF DESCRIPTION OF THE DRAWINGS

The invention will be further elucidated in the figures.

DETAILED DESCRIPTION

Aspects of the invention relate to a dielectric barrier discharge plasma treatment pad with a treatment zone having a pattern of one or more active areas and a complementary pattern of non-active areas, such that a complementary part of a surface to be treated is covered by the one or more active areas when the treatment pad is reapplied on the object with an offset, e.g. a translation or rotation in plane of the treatment zone. The benefit is that in this way relatively large surfaces can be treated, with the advantages of having relatively small and flexible electrodes.

With the pattern of one or more active areas and the complementary pattern of non-active areas forming an alternating pattern, a relatively large degree of variations in shapes of the treatment zone, pattern shapes and types of offsets can be used to provide plasma treatment to a surface to be treated. This may provide the user or clinician with treatment options tailored to the need of the patient.

In some preferred embodiments, the pattern comprises one or more elongate active areas and an equal number of non-active areas, e.g. forming a parallel pattern. The elongate active areas have a long side oriented along a lateral direction and a short side oriented along a horizontal direction. The active areas and non-active areas are preferably arranged serially along the horizontal direction. By this, a minimal creepage distance between active areas can be ensured to comply with electrical safety requirements. Additionally, two or more elongate active areas can be equal in size, to have uniform treatment characteristics of active areas along the treatment zone.

Preferably, the treatment pad is reapplied on the object with an offset being a rotation in plane of the treatment zone of one hundred and eighty degrees, e.g. for ease-of-use of the clinician.

In preferred embodiments, the treatment pad further comprises a set of reference markers, each arranged for marking a position on a side of the surface to be treated. The treatment pad can comprise flaps symmetrically extending outward from the treatment zone in a border portion the treatment pad, to engage with the set of reference markers. The reference markers can for example be circular reference stickers with a radius of curvature matching a radius of curvature of cylindrically rounded notches on the flaps of the pad, to provide a means for realigning the treatment pad, such that the complementary part of the surface to be treated is covered by the one or more active areas when the treatment pad is reapplied on the object with an offset.

In some embodiments, the treatment pad further comprises a pad sticker having an adhesive material to attach the treatment pad to the object, e.g. a patient or surface to be disinfected or sterilized. Preferably, an outer contour of the pad sticker at least exposes the set of reference markers, to enable to visually check the alignment of the treatment pad on the object after it has been attached.

In other or further embodiments, the treatment pad comprises an edge around a circumference of the treatment zone, to create a sealed contact between the treatment pad and the object to prevent airflow between the surroundings and the active areas and to improve electrical safety of the pad.

Other aspects of the invention pertain to a control unit for controlling the treatment pad as disclosed herein, comprising a controller and a high voltage power source for controlling the voltage to the one or more active areas. The controller is arranged for activating a pattern of one or more active areas when the treatment pad is first applied on the object, and for activating a superset, set or subset of active areas in the pattern of one or more active areas such that a complementary part of the surface to be treated is covered by the subset of active areas when the treatment pad is reapplied on the object with an offset. In case of partial overlap or misalignment of the pattern, this allows activating only those active areas that form the complementary part of the surface to be treated, to avoid the risk that parts of the surface are undertreated or overtreated. A superset may encompass the set or subset.

By having the controller additionally arranged for sequentially activating active areas, exceeding a total output voltage limit of the treatment pad can be avoided. Additionally the controller can be arranged for having the pattern of one or more active areas provide a dielectric barrier plasma to the surface to be treated with a predefined first duration and intensity when the treatment pad is first applied on the object, and for having the pattern of one or more active areas provide a dielectric barrier plasma to the surface to be treated with a matching second duration and intensity when the treatment pad is reapplied on the object with an offset. This promotes that all parts of the surface to be treated are provided with an equal dose of plasma.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 1:
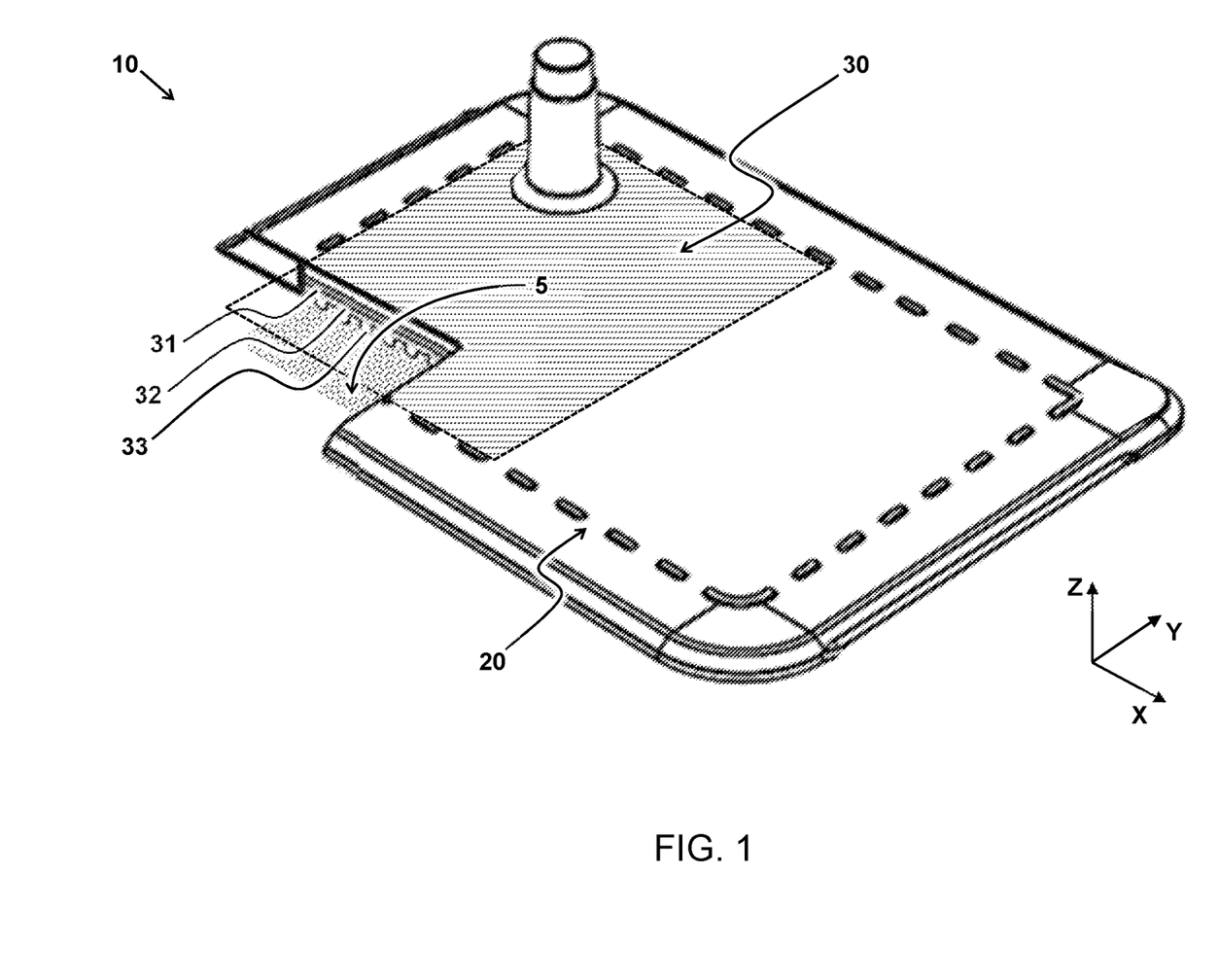
FIG. 1 illustrates an isometric view of a treatment pad.

FIG. 1 illustrates an isometric view of a treatment pad 10 for a dielectric barrier discharge plasma treatment of a surface 5 to be treated of an electrically conducting body, which surface 5 is used as a counter electrode. In a preferred embodiment, the treatment pad 10 comprises a treatment zone 20, arranged for at least covering the surface 5 to be treated. The treatment zone 20 can be rectangular, as shown in FIG. 1, or a different geometrical or irregular shape that covers the surface 5 to be treated. The treatment pad 10 further comprises a pattern of one or more active areas 30, integrated in the treatment zone 20 and arranged for generating a dielectric barrier discharge plasma. Preferably, each of the one or more active areas 30 comprises a first electrode 31, a dielectric 32, and a spacer 33. The first electrode 31 is to be coupled to a high voltage power source. This may be carried out simultaneously for all active areas in the treatment pad, or may be carried out sequentially; e.g. by manually connecting a high voltage source to an electrode 31 via a terminal clamp or the like. In other embodiments, active areas may be interconnected via connecting conductors integrated in the treatment pad or each active area may have an individual connecting terminal pin. The dielectric 32 is formed by a coating or foil of a flexible material so that the dielectric 32 shields the first electrode 31 from the surface 5 to be treated. The spacer 33 comprises a structured surface of protrusions adjacent a side of the dielectric 32 facing the surface 5 to be treated. In some embodiments, the dielectric 32 and spacer 33 span at least part of the treatment zone 20 and are shared by multiple active areas 30, while each active area 30 comprises an individual first electrode 31. By each having a first electrode 31, the active areas 30 can be activated independently from each other, for example by connecting, in a specific order, first electrodes 31 of active areas 30 to a high voltage power source. Alternatively, multiple active areas 30 can be activated simultaneously, by having their first electrodes 31 simultaneously powered by a high voltage power source. Activating the active areas 30 and/or setting the order in which the active areas 30 are activated can be a manual process or a (semi)automated process. In a preferred embodiment, the treatment zone 20 comprises a complementary pattern of non-active areas, such that a complementary part of the surface 5 to be treated is covered by the said one or more active areas 30 when the treatment pad 10 is reapplied on the object with an offset.

The benefit of a treatment pad 10 such as the embodiment shown in FIG. 1 is that it can provide relatively large surfaces with dielectric barrier discharge plasma treatment, without the risk that parts of the surface are undertreated or overtreated and without the effects of capacitive loading.

In some embodiments, as shown in FIGS. 2-5, the treatment pad 10 comprises a treatment zone 20 with a pattern of one or more active areas 30 and a complementary pattern of non-active areas forming an alternating pattern of active areas 30 and non-active areas. The purpose of the embodiments shown in FIGS. 2-5 is to schematically illustrate potential variations of these patterns, without being limited to the specific pattern as depicted. Also, obviously, realistic patterns are constrained by plasma forming properties e.g. regarding sharp edges. Also, no specific format is provided for the active area, as long as it is able to provide the plasma forming effect.

Figure 2:
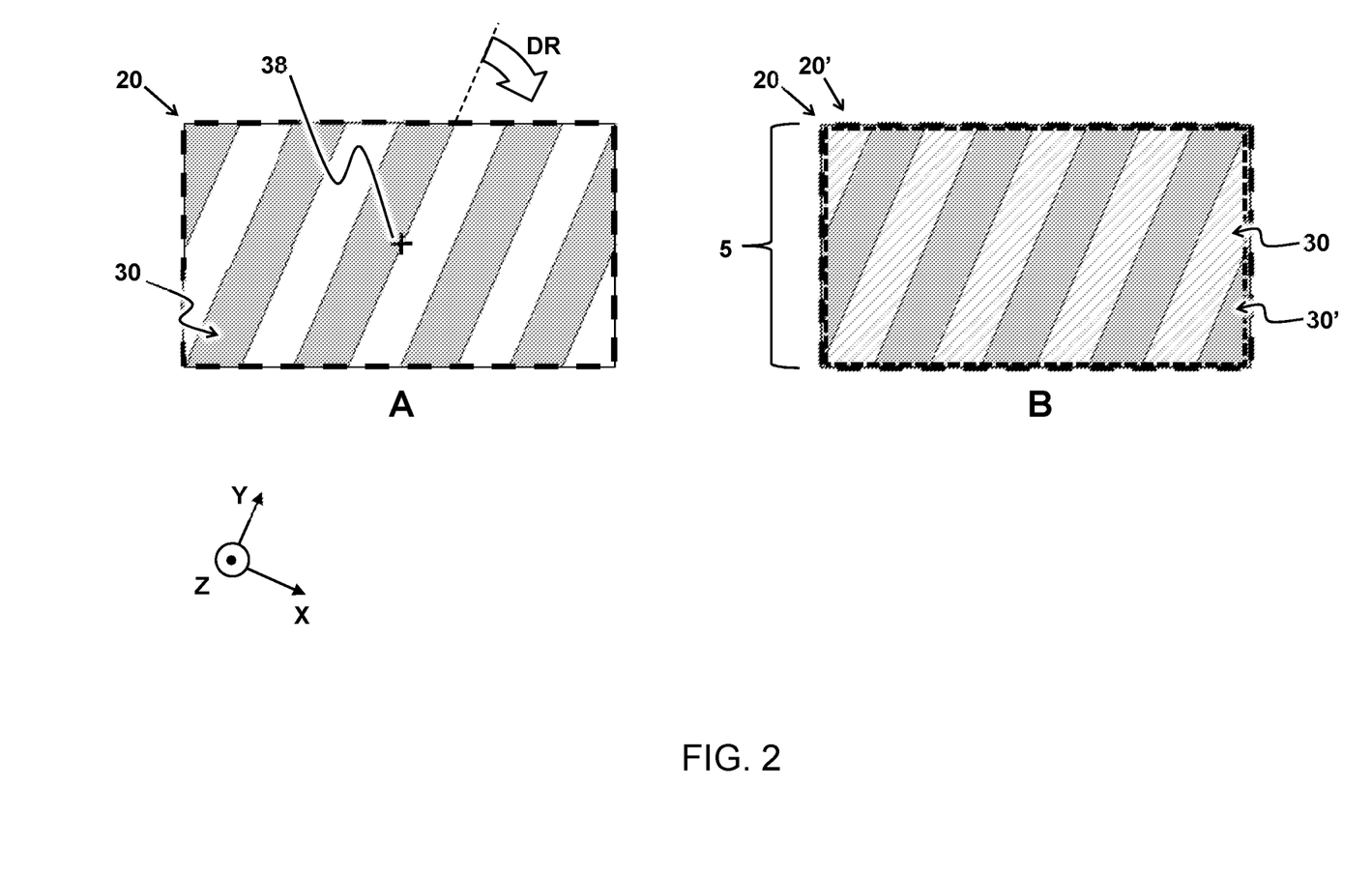
FIG. 2 illustrates a detailed view of a pattern of active areas.

FIG. 2 illustrates a detailed view of a pattern of active areas 30. As shown in FIG. 2A, the pattern comprises one or more elongate active areas 30 and an equal number of non-active areas. By having an equal number of active areas 30 and non-active areas, a complementary part of the surface 5 to be treated can be covered by the active areas 30 when the treatment pad 10 is reapplied on the object with an offset, without active areas 30 covering a part of the object beyond the surface 5 to be treated. Accordingly, the size of the treatment pad 10 can be closely matched with the size of the surface 5 to be treated.

Alternatively, the pattern can comprise an unequal number of active areas 30 and non-active areas. For patterns comprising more active areas 30 than non-active areas, a number of active areas 30 would cover a part of the object beyond the surface 5 to be treated when the treatment pad 10 is reapplied on the object with an offset. To avoid providing plasma to parts of the object beyond the surface 5 to be treated, a superset or subset of the pattern of active areas 30 covering the surface 5 to be treated can be activated, while the remaining active areas 30 (not covering the surface 5 to be treated) are deactivated.

For patterns comprising fewer active areas 30 than non-active areas, the treatment pad 10 can be reapplied on the object with an offset multiple time, e.g. an incremental offset, such as a stepwise rotation or translation or combination thereof, until the entire surface 5 to be treated has been covered by the pattern of active areas 30.

As shown in FIG. 2, the active areas 30 have a long side oriented along a lateral direction Y and a short side oriented along a horizontal direction X. The active areas 30 and non-active areas are arranged serially along the horizontal direction X, e.g. forming a parallel pattern. The orientation of treatment zone 20 does not necessarily need to be aligned with the orientation of active areas 30.

Alternatively, the active areas 30 can have a long side oriented along the horizontal direction X and a short side oriented along the lateral direction Y.

Additionally, or alternatively, the elongate active areas 30 can be curved, e.g. have a sinusoidal shape with peaks forming the short side, e.g. waves moving in the horizontal direction X.

A potential benefit of a parallel pattern is that elongate active areas 30 are spaced apart with a uniform interdistance along their long side, which can ensure a minimal creepage distance between active areas 30 to comply with electrical safety requirements, such as IEC 60601-1 for medical devices.

In a preferred embodiment, two or more elongate active areas 30 are equal in size. For example, in a pattern comprising more than one active area 30, all active areas 30 can be equal in size, or a subset of all active areas 30 can be equal in size, or at least two active areas 30 can be equal in size. Having active areas 30 equal in size promotes equal operating characteristics, such as the generation of plasma and the effects of capacitive loading, which can be important usability, safety or control parameters.

Preferably, the treatment pad 10 is reapplied on the object with an angular offset, being a rotation in plane of the treatment zone 20 of one hundred and eighty degrees. This has been found to be most user-friendly (to the clinician), because of a relatively easy re-alignment procedure.

FIG. 2A shows the pattern of elongate active areas 30 and the complementary pattern of active areas 30' when the treatment zone 20' is reapplied on the object with an angular offset DR of one hundred and eighty degrees around a central origin 38.

Accordingly, the rotated treatment zone 20' is realigned with the original treatment zone 20. As a result, the surface 5 to be treated can effectively be equal to or smaller than the treatment zone 20.

The treatment zone 20 can alternatively be a different geometrical or irregular shape and the offset can alternatively be a translation of the pattern along the short side of the active areas 30, though this may reduce the effective size of the surface 5 to be treated.

In FIG. 3A, the treatment zone 20 is rectangular and comprises a two-dimensional alternating pattern of a plurality of rectangularly shaped active areas 30 and complementary non-active areas, e.g. forming a checkerboard pattern.

In some embodiments, the first electrodes 31 of adjacent active areas 30 are electrically isolated from each other and each of the active areas 30 comprises an electrode connector to connect its first electrode 31 to a high voltage power source for independent activation of active areas 30.

Alternatively, the first electrodes 31 of selected active areas 30 can be electrically connected to each other, e.g. to form a predefined subset of active areas 30 comprising a shared electrode connector for combined activation of active areas 30. The predefined subset of electrically connected active areas 30 may comprise active areas 30 that are topographically separated, e.g. having at least a horizontal distance of 2W in the horizontal direction X and a lateral distance 2H in the lateral direction Y between active areas 30 in a subset.

The complementary part of the surface 5 to be treated, shown in FIG. 3B, can be covered by translating the treatment zone 20 along the lateral direction DY. When the treatment zone 20' is reapplied on the object, the active areas 30' are shifted along the lateral direction DY by a height H of an active area 30. This creates a row of alternating active areas 30, 30' and non-active areas on two opposing edges of the surface 5 to be treated. As a result, the surface 5 to be treated is effectively smaller than the treatment zone 20.

With respect to the embodiment of FIG. 3, steps for providing plasma treatment to the surface 5 to be treated can e.g. be as follows. At the start of the procedure the treatment zone 20 is first applied on an object, with a first set or subset of the pattern of active areas 30 covering a first part of the surface 5 to be treated. Specific sets or subsets of active areas 30 can e.g. be activated by having active areas 30 of which the first electrodes 31 are electrically isolated from each other and that comprise individual electrode connectors to connect the active areas 30 to a high voltage power source. As shown in FIG. 3A, the first subset comprises the top three rows of active areas 30 in treatment zone 20. Accordingly, the first subset of active areas 30 is activated to provide a dielectric barrier discharge plasma to the first part of the surface 5 to be treated. In the checkerboard pattern, active areas that are adjacent may be activated sequentially e.g. to limit capacitive loading in the active areas.

Next, the treatment zone 20 is reapplied on the object with a translation along DY by a height H of an active area. This causes a second subset of the pattern of active areas 30' to cover a second part of the surface 5 to be treated, complementary to the first part of the surface 5 to be treated. As shown in FIG. 3B, the second subset comprises the bottom three rows of active areas 30' in treatment zone 20'. Finally, the second subset of active areas 30' is activated to provide a dielectric barrier discharge plasma to the complementary part of the surface 5 to be treated. Also, here, active areas may be activated sequentially or simultaneously if possible.

Alternatively, the complementary part of the surface 5 to be treated can be covered by translating the treatment zone along the horizontal direction, perpendicular to the lateral direction DY in plane of the treatment zone 20. Accordingly, the treatment zone 20' is reapplied on the object, with the active areas 30' shifted by a width W of an active area 30.

The treatment zone 20 can alternatively be a different geometrical or irregular shape, and the checkerboard pattern of active areas 30 can comprise an odd or even number or rows or columns.

Additionally, or alternatively, the orientation of the active areas 30 can be tilted relative to the orientation of the treatment zone 20, and within the treatment zone 20 the active areas 30 may vary in size.

Figure 4:
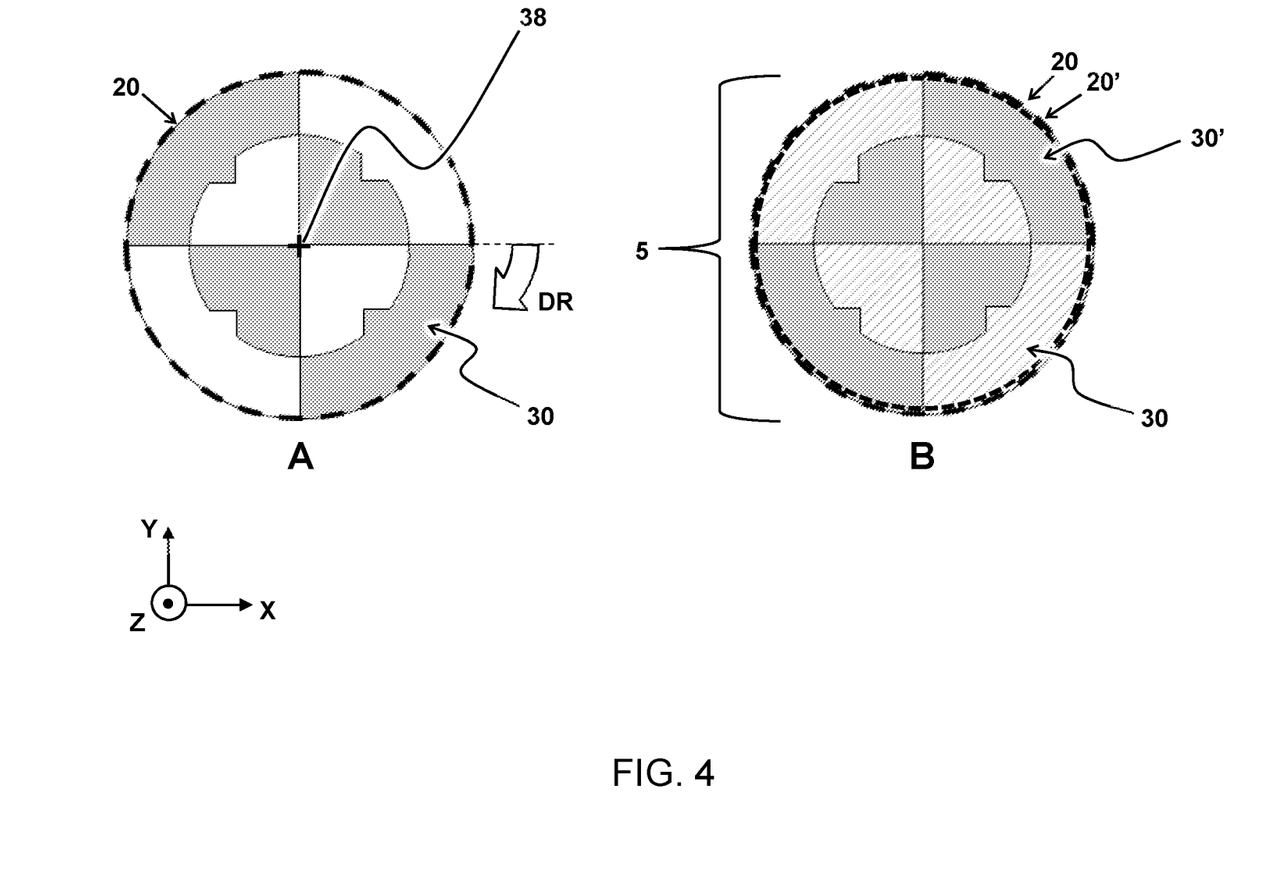
FIG. 4 illustrates a detailed view of another pattern of active areas.

FIG. 4 illustrates a detailed view of another pattern of active areas 30. FIG. 4A shows a circular treatment zone 20 with an alternating pattern of active areas 30 and complementary non-active areas aligned with respect to a central origin 38, e.g. forming a cloverleaf pattern. With this pattern, the complementary part of the surface 5 to be treated can be covered by the active areas 30' by rotating the treatment zone 20 along an angular offset DR in plane of the surface 5 to be treated of ninety degrees, either clockwise or counter-clockwise. When the treatment zone 20' is reapplied on the object, as shown in FIG. 4B, the rotated treatment zone 20' is aligned with the original treatment zone 20. As a result, the surface 5 to be treated can effectively be equal to or smaller than the treatment zone 20.

Alternatively, the pattern of active areas 30 shown in FIG. 4A can comprise less or more active areas 30 and complementary non-active areas. Alternatively, the pattern can comprise regularly or irregularly divided circle segments, with or without notches, e.g. forming a dartboard pattern. In some embodiments, the active areas 30 comprise first electrodes 31 that are electrically isolated from each other, e.g. to allow activation of subsets.

Figure 5:
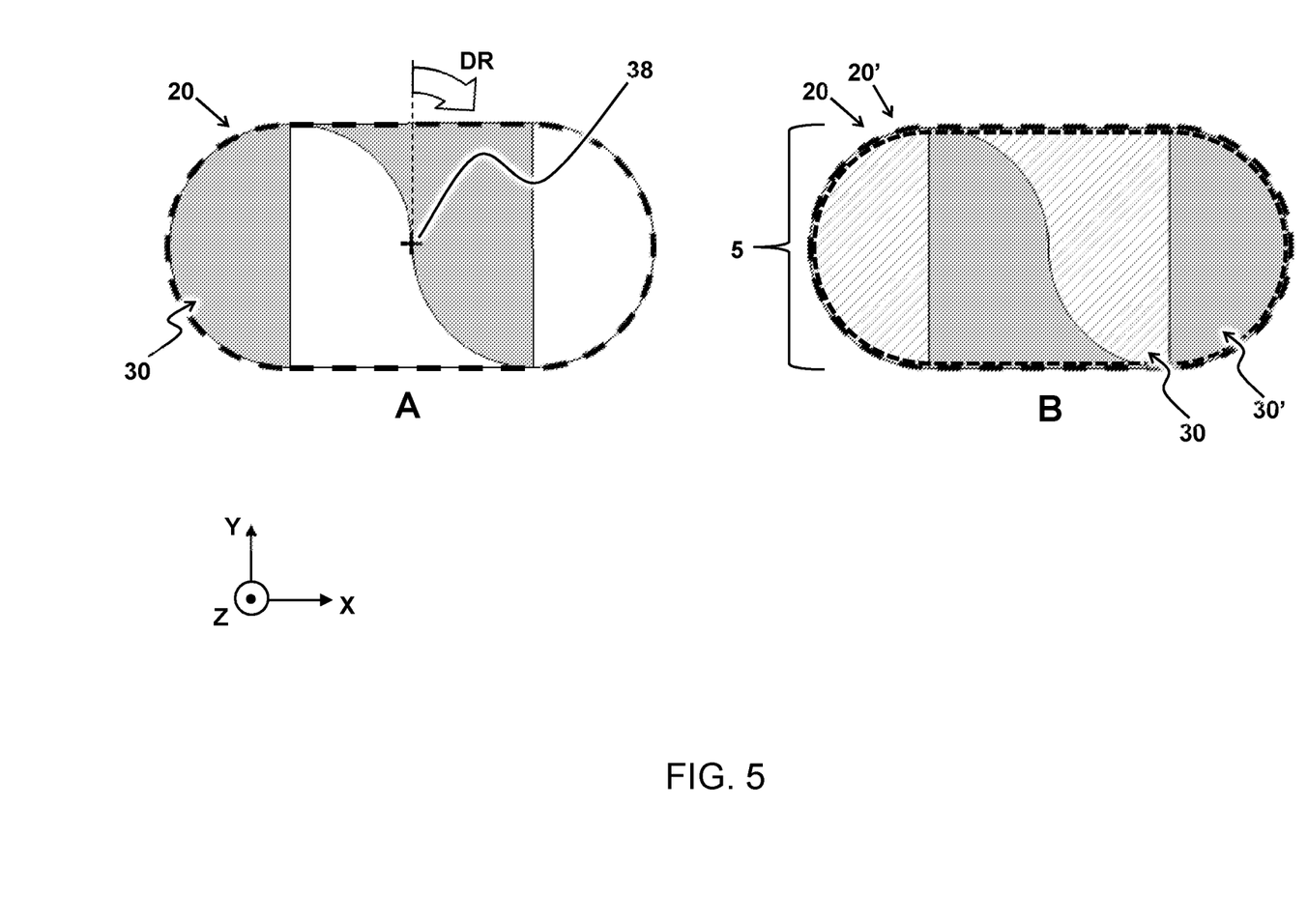
FIG. 5 illustrates a detailed view of another pattern of active areas.

In the embodiment shown in FIG. 5, the treatment zone 20 is elongated with rounded ends, and comprises an alternating pattern of active areas 30 and complementary non-active areas, in which the active areas 30 have different shapes and sizes, e.g. forming a band-aid pattern. The active areas 30 comprise rounded edges to follow the contour of the treatment zone 20 and to create a sinusoidal boundary, crossing a central origin 38, between an active area 30 and a non-active area, as can be seen in FIG. 5A. Active areas 30 may comprise first electrodes 31 that are electrically isolated from each other, e.g. to allow activation of subsets.

FIG. 5B shows the treatment zone 20' when the treatment pad 10 is reapplied on the object with an angular offset DR. The original treatment zone 20 can be rotated around the central origin 38 by one hundred and eighty degrees and reapplied on the surface 5 to be treated. The corresponding complementary pattern of active areas 30' on the rotated treatment zone 20' is able to entirely cover a surface 5 to be treated that is equal to or smaller than the treatment zone 20.

Figure 6:
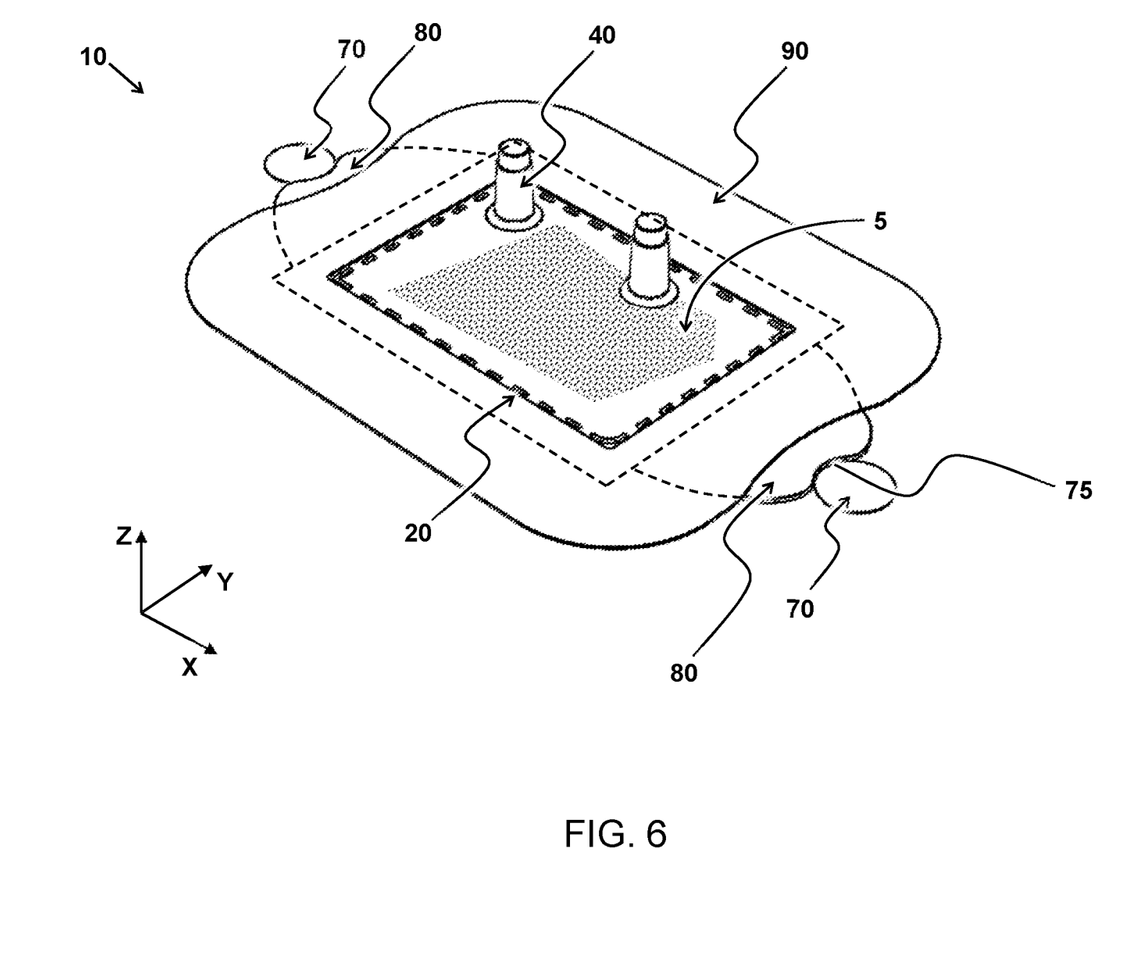
FIG. 6 illustrates further features of the treatment pad.

FIG. 6 illustrates further features of the treatment pad 10. As shown, the treatment pad 10 further comprises a set of reference markers 70, each arranged for marking a position on a side of the surface 5 to be treated. The reference markers 70 can for example be placed on opposing sides of the surface 5 to be treated, as shown in FIG. 6. By marking a position on a side of the surface 5 to be treated, the treatment pad 10 can be realigned with respect to the reference markers 70 when the treatment pad 10 is reapplied on the object with an offset.

Alternatively, the set of reference markers 70 can be arranged on adjacent sides of the surface 5 to be treated, or the set of reference markers 70 can be arranged on one side of the surface 5 to be treated. However, it is recommended that the marked distance between reference markers 70 is as large as practically possible, because this decreases the risk of alignment error when the treatment pad 10 is reapplied on the object.

In another or further embodiment, a first reference marker 70 can be arranged for marking a position corresponding to a center of rotation for an angular offset of the treatment pad 10. A second and third reference marker 70 can be used for defining an initial orientation of the treatment pad 10, and an orientation of the treatment pad 10 when it is reapplied on the object with an angular offset, respectively.

Figure 7:
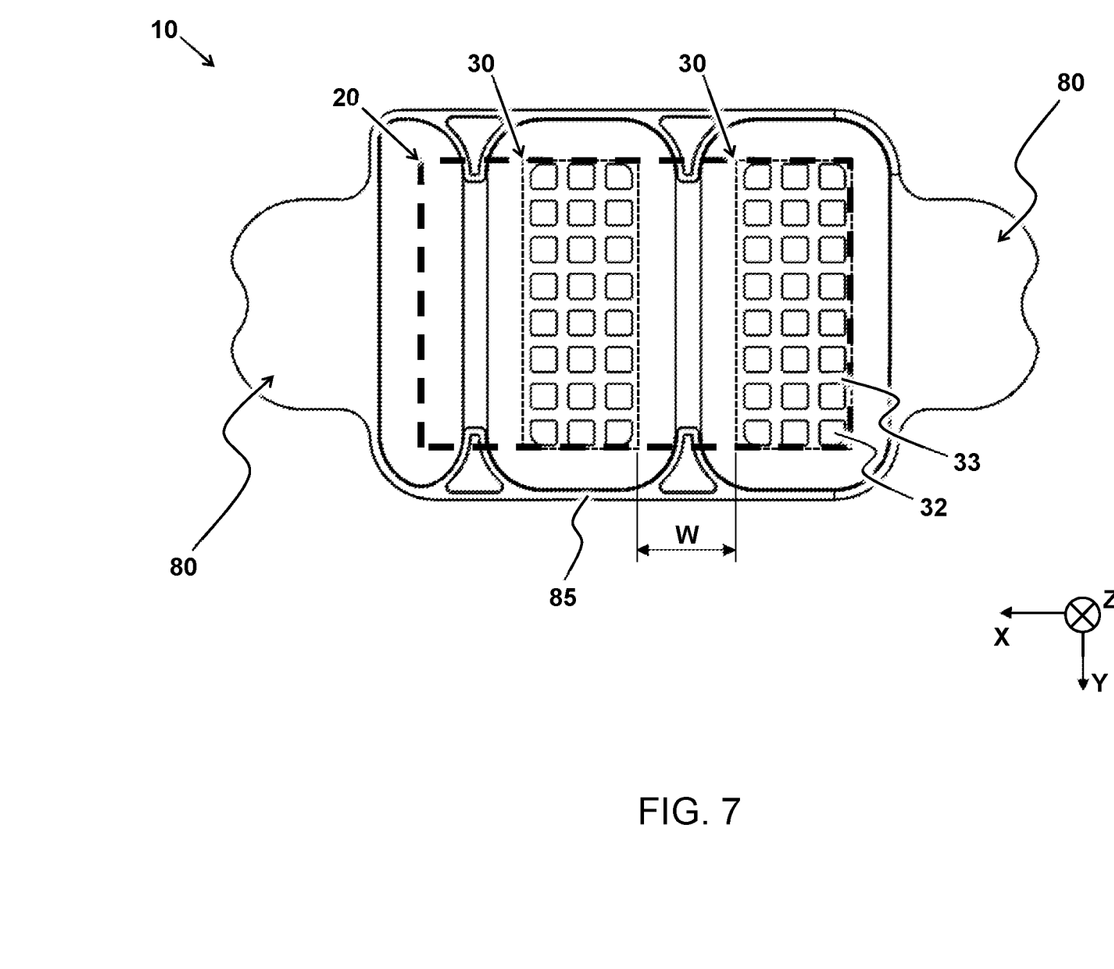
FIG. 7 illustrates a bottom view of the treatment pad.

Preferably, the treatment pad 10 comprises flaps 80 symmetrically extending outward from the treatment zone 20 to engage with the set of reference markers 70. For example, as shown in FIG. 6 and FIG. 7, the flaps 80 extend from opposing sides of the treatment zone 20 toward the reference markers 70.

Alternatively, in combination with sets of reference markers 70 prescribed to be arranged e.g. on adjacent sides or on one side, the flaps 80 can extend from sides of the treatment zone 20 that correspond with the prescribed position of the reference markers 70.

In some embodiments, for example as shown in FIG. 6, the reference markers 70 are circular reference stickers with a radius of curvature matching a radius of curvature of cylindrically rounded notches 75 on the flaps 80 of the pad 10. The matching radii of curvature can thus be used to realign the treatment pad 10 with the reference markers 10 when the treatment pad 10 is reapplied on the object with an offset.

Alignment can for example be done visually. In other embodiments, alignment is done mechanically by having reference markers 70 and flaps 80 with a substantial thickness, e.g. a thickness at least two millimeters, preferably between two and five millimeters. When the reference marker 70 and the flap 80 are mechanically aligned, this can additionally provide in-plane stability of the treatment pad 10 relative to the object during a dielectric barrier discharge plasma treatment session, which may reduce the risk that parts of the surface are undertreated or overtreated.

Alternatively, mechanical alignment between the reference markers 70 and the treatment pad 10 can comprise engaging elements, e.g. forming a click system. For example, the reference markers 70 can have a mushroom shape, i.e. with a base portion having a relatively small diameter which is attached to the skin of the patient, and an upper portion having a relatively large diameter. The diameter of the base portion can be used to align the reference marker 70 with a cylindrically rounded notch 75 in plane of the treatment zone relative to the object, and the diameter of the upper portion protruding over the flap 80 can constrain vertical movement of the treatment zone relative to the object.

Instead of being circular, the reference markers 70 can comprise a different predefined geometrical shape, e.g. arrow, diamond, hexagon, triangle or rectangle, matching a notch 75 on a flap 80 on the treatment pad 10.

Alternatively, the flap 80 may extend beyond the reference marker 70. Instead of a notch 75, the flap 80 may comprise an indent from a bottom surface of the flap 80, with the indent having a shape matching the shape of the reference marker 70 to provide an alignment means. The indent preferably has a height larger than the thickness of the reference marker 70. Alternatively, the indent can be a through-hole, running from a bottom surface of the flap 80 to a top surface of the flap 80.

In another or further preferred embodiment, the treatment pad 10 comprises a pad sticker 90 having an adhesive material to attach the treatment pad 10 to the object, as can be seen in FIG. 6. For example, the pad sticker 90 has a central cutout to expose the projected top of the treatment zone 20 and to allow access to the electrode connectors 40. In some embodiments, the outer contour of the pad sticker 90 at least exposes the notches 75 on the flaps 80, so that alignment of the treatment pad 10 with the reference markers 70 can be checked visually. Preferably, the pad sticker 90 does not cover or adhere to the reference markers 70, to improve usability and to avoid removing the reference markers 70 from the skin of the patient when the treatment pad is reapplied with an offset.

Alternatively, the pad sticker 90 covers the reference markers 70 and is at least partially transparent to allow visual alignment of the treatment pad 10 with the reference markers 70.

As shown in FIG. 6, an inner portion of the pad sticker 90 is attached to a top surface of the treatment pad 10, and an outer portion of the pad sticker 90 is attached to the object, e.g. the skin of a patient. Alternatively, the pad sticker 90 can e.g. be a double-sided adhesive sticker attaching a bottom surface of the treatment pad 10 to the object.

Additionally, or alternatively, the pad sticker 90 can be used to attach flaps 80 to the object, e.g. by a double-sided adhesive on a bottom surface of flaps 80. Alternatively, the functionalities of flaps 80 and pad sticker 90 can be integrated. For example, the flaps 80 can have an adhesive material to attach the treatment pad 10 to the object, or the pad sticker 90 can be an integral part of the treatment pad 10 and have notches 75 with a radius of curvature matching a radius of curvature of circular reference markers 70.

Preferably, the adhesive material is friendly to sensitive and elderly skin, to avoid irritation or allergic reactions.

Preferably the adhesive material allows multiple reapplications of the pad sticker 90, to reattach the treatment pad 10 to the object when the treatment pad 10 is reapplied on the object with an offset.

Instead of being a single ring-shaped sticker, as shown in FIG. 6, the pad sticker 90 can comprise a set of multiple stickers to attach the treatment pad 10 to the object, for example having stickers attached to corners or edges of the pad 10.

FIG. 7 illustrates a bottom view of the treatment pad 10. In another or further embodiment as shown, the treatment pad 10 further comprises an edge 85 around a circumference of the treatment zone 20, e.g. a rectangular or circular edge depending on the shape of the treatment zone 20, to create a sealed contact between the treatment pad 10 and the object to prevent airflow between the surroundings and the active areas 30 and to improve electrical safety of the treatment pad 10, e.g. to comply to medical device regulations. Each active area 30 is arranged for generating a dielectric barrier discharge plasma and comprises a first electrode 31 (see FIG. 1), a dielectric 32, and a spacer 33 comprising a structured surface of protrusions. The thickness of the spacer 33 defines the distance between the dielectric 32 and the surface 5 to be treated, to ensure sufficient air is available in the cavity to convert to plasma, to reduce the risk of contact between the dielectric 32 and the surface 5 to be treated, and to reduce the risk of wound fluid filling the cavity. A larger thickness of the spacer 33 creates a larger offset between the first electrode 31 and the surface 5 to be treated, which in turn may increase the voltage required to generate plasma in the cavity. For example, the spacer 33 has a thickness of more than half a millimeter, preferably between half a millimeter and three millimeters, more preferably between half a millimeter and one and a half millimeter.

As shown in FIG. 7, the edge 85 can for example be an integrally formed part with flaps 80. Preferably, the edge 85 forms a seal around the treatment zone 20 with a sufficient margin of distance (i.e. a minimum creepage distance) between the first electrode(s) and the edge of the treatment pad for electrical safety of the treatment pad 10.

In some embodiments, the edge 85 comprises an adhesive material to attach the treatment pad 10 to the object.

Preferably, the distance W between adjacent active areas 30 is at least ten millimeters, preferably between ten and eighty millimeters, most preferably between fifteen and fifty millimeters. This ensures a minimum distance between adjacent active areas 30, e.g. to make sure an electrode connector of a non-activated active area 30 is safe to touch, which may be required to comply to technical standards such as IEC 60601-1 for medical devices. Alternatively, when the active areas 30 are provided with additional electrical isolation means, the minimum distance between active areas 30 can be smaller. In some embodiments, an additional distance of e.g. between one and three millimeters, preferably one millimeter, is added between active areas 30 and non-active areas, to allow for manual placement tolerances when repositioning the pad.

Additionally, this provides a scalable pattern of active areas 30 in which the size of active areas 30 limits capacitive loading. Thus, when treating relatively large surfaces 5, the present invention may not require changes to the output voltage of the treatment pad 10 to successfully ignite the plasma.

This may offer perspectives for medical treatments and prevention measures for larger wounds. In dermatology, new opportunities can be opened for wound healing, tissue regeneration, therapy of skin infections, and probably many more applications.

In preferred embodiments, the treatment pad 10 comprises a treatment zone 20 arranged for covering a surface 5 to be treated that is larger than one thousand two hundred millimeter squared. For example, a surface 5 to be treated between one thousand two hundred millimeter squared and sixty thousand millimeter squared, preferably between two thousand four hundred millimeter squared and ten thousand millimeter squared.

These large surface areas can be found in the treatment of skin diseases, such as bacterial or fungal infections, or chronic wounds and inflammations. Plasmas may very well assist in controlling the consequences of chronic inflammation associated with these diseases by eliminating bacterial and fungal infections, which results in a drastic improvement of the quality of life.

Secondly, having these large surface areas available for dielectric barrier discharge plasma treatment may benefit hospital hygiene by sterilizing or disinfecting medical equipment and body parts (e.g. of surgeons).

Figure 8:
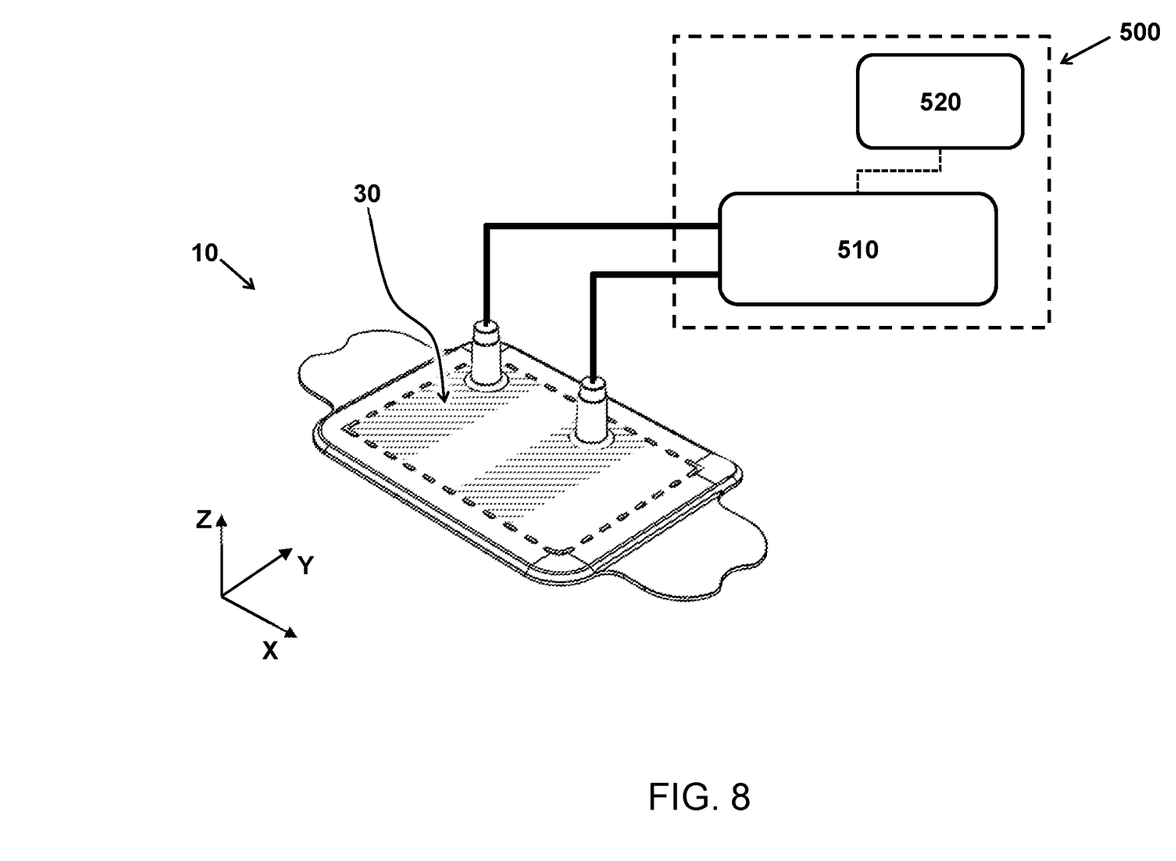
FIG. 8 illustrates a control unit (500) for controlling the treatment pad.
Figure 9:
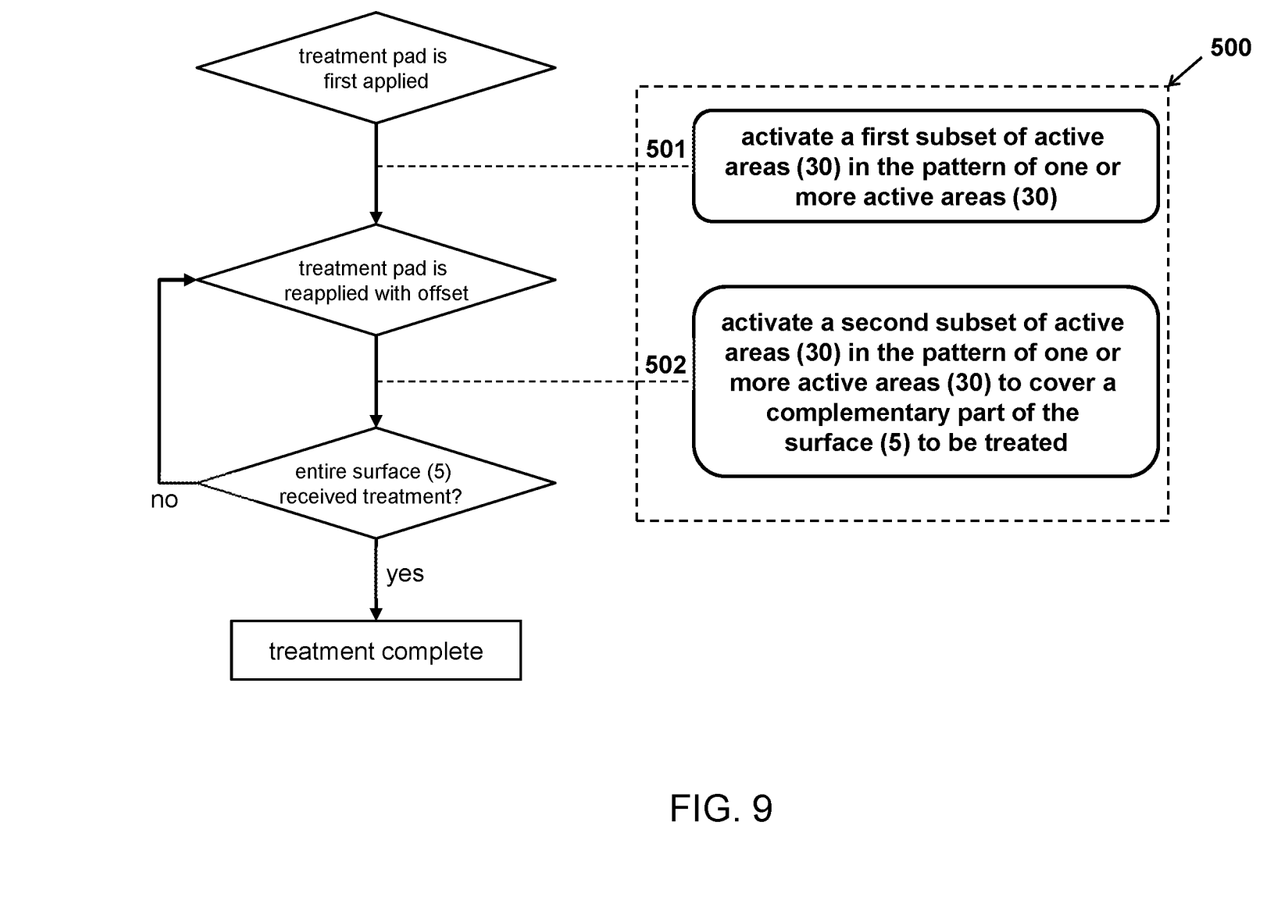
FIG. 9 illustrates a control scheme for the control unit of FIG. 8.

FIG. 8 illustrates a control unit 500 for controlling the treatment pad 10, with a control scheme for the control unit 500 shown in FIG. 9. In a preferred embodiment, the control unit comprises a controller 520 and a high voltage power source 510 for controlling the voltage to the one or more active areas 30. Preferably, the controller 520 is arranged for activating a first subset of active areas 30 in the pattern of one or more active areas 30 when the treatment pad 10 is first applied on the object, e.g. a number of active areas 30 that cover a specific area of the surface 5 to be treated are initially activated from the pattern of active areas 30. Preferably, the controller 520 is further arranged for activating a second subset of active areas 30 in the pattern of one or more active areas 30 such that a complementary part of the surface 5 to be treated is covered by the subset of active areas 30 when the treatment pad 10 is reapplied on the object with an offset. The second subset e.g. is a number of active areas 30 that cover another area of the surface 5 to be treated, complementary to the initially covered area of the surface 5 to be treated.

Figure 3:
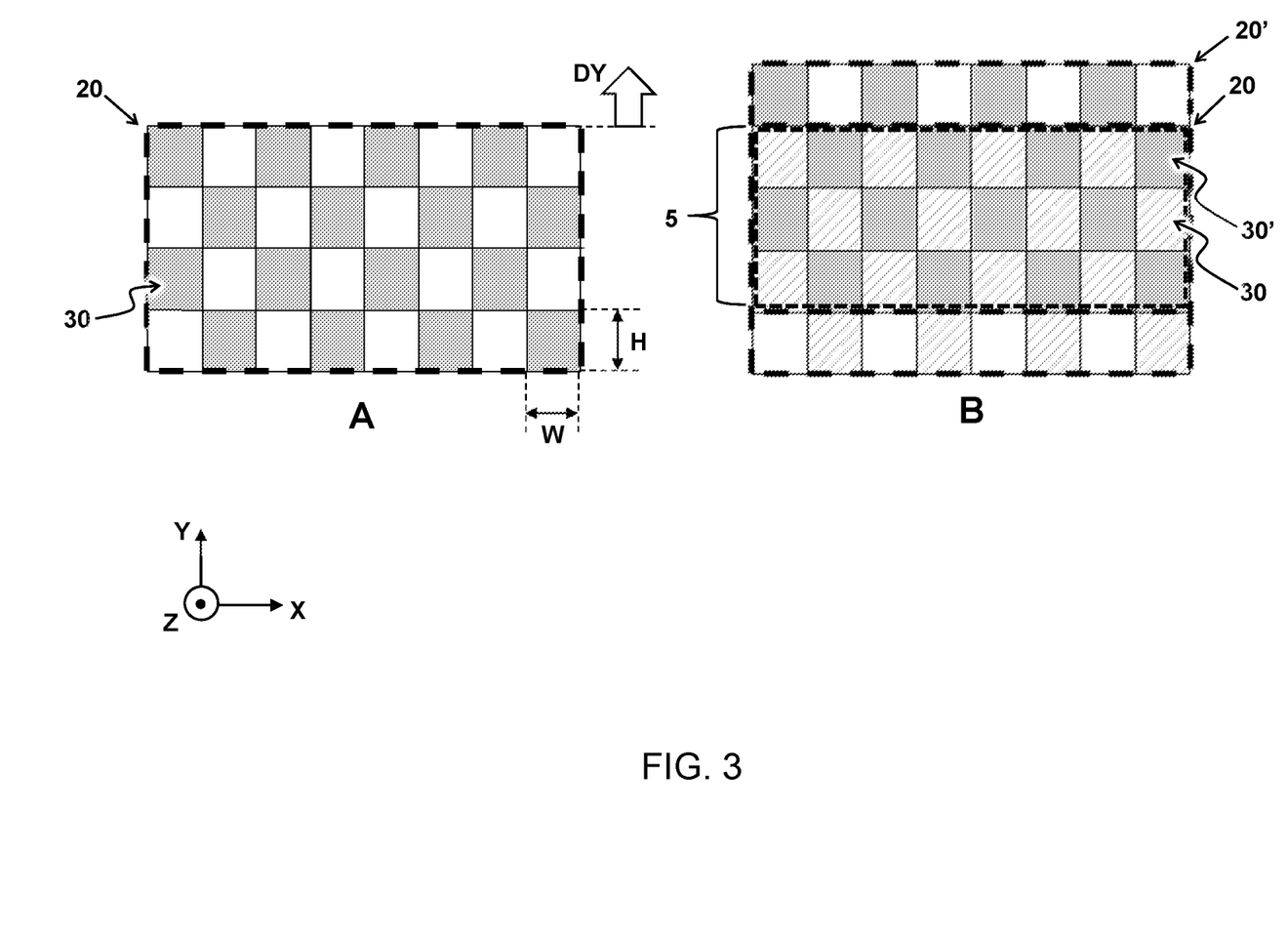
FIG. 3 illustrates a detailed view of another pattern of active areas.

This can for example be used when the offset is a translation and a number of active areas 30 do not cover the surface 5 to be treated, as illustrated in FIG. 3.

More than two subsets of active areas 30 may be required to cover the entire surface 5 to be treated. Accordingly, the treatment pad 10 may be reapplied on the object an equal number of times.

Alternatively, different subsets of active areas 30 can be activated in a number of treatment steps while the treatment pad 10 remains in position on the object to be treated, e.g. to limit capacitive loading by having smaller subsets of active areas 30, or to treat larger wounds without being limited by capacitive loading.

In some embodiments, the control unit 500 comprises a controller 520 that is additionally arranged for sequentially activating active areas 30 to avoid exceeding a total output voltage limit of the treatment pad 10.

The controller can be arranged to activate active areas 30 in a predefined optimal order, e.g. to limit capacitive loading, to limit local increase in temperature of the treatment pad 10 or of the surface 5 to be treated, or to improve treatment effectiveness. Alternatively, or additionally, the predefined optimal order of activating the active areas 30 can be based on the layout of the wound or the anatomy of the affected body part, e.g. by activating a subset of active areas 30 that cover the surface 5 to be treated.

In other or further embodiments, the control unit 500 comprises a controller 520 that is additionally arranged for having the pattern of one or more active areas 30 provide a dielectric barrier plasma to the surface 5 to be treated with a predefined first duration and intensity when the treatment pad 10 is first applied on the object, and for having the pattern of one or more active areas 30 provide a dielectric barrier plasma to the surface 5 to be treated with a matching second duration and intensity when the treatment pad 10 is reapplied on the object with an offset. This can promote that the plasma dose is equally distributed to the surface 5 to be treated.

Alternatively, the controller 520 can be arranged for having the second duration and/or intensity differ from the first duration and/or intensity, e.g. to provide a varying dose of plasma treatment, based on varying degrees of disease of regions within the wound.

FIG. 9 illustrates a control scheme for the control unit 500 of FIG. 8. The procedure is started by a user (e.g. a clinician) first applying the treatment pad 10 on an object. Next, the control unit 500 is provided with a signal to activate the pattern of one or more active areas 30 (step 501), to provide a first dielectric barrier discharge plasma treatment to the surface 5 to be treated.

When step 501 is done, the user reapplies the treatment pad 10 on the object with an offset. Next, control unit 500 is provided with a signal to activate a subset in the pattern of one or more active areas 30 to cover a complementary part of the surface 5 to be treated (step 502).

When step 502 is done, the user verifies if the entire surface 5 to be treated has successfully received plasma treatment. If this is true, the treatment is complete. If this is not true, the steps of reapplying the treatment pad 10 on the object with an offset and step 502 of the control unit 500 are repeated, until the outcome of the verification step is positive.

The invention also relates to a treatment pad for a dielectric barrier discharge plasma treatment of a surface to be treated of an electrically conducting body, which surface is used as a counter electrode, said treatment pad comprising:
  a treatment surface, arranged for at least covering the surface to be treated;
  a pattern of one or more active areas, integrated in the treatment surface and arranged for generating a dielectric barrier discharge plasma, each said one or more active areas comprising:
    a first electrode to be coupled to a high voltage power source;
    a dielectric formed by a coating or foil of a flexible material so that the dielectric shields the first electrode from the surface to be treated; and a spacer comprising a structured surface of protrusions adjacent a side of the dielectric facing the surface to be treated;

wherein the treatment surface comprises a complementary pattern of non-active areas, is covered by the said one or more active areas when the treatment pad is reapplied on the object with an offset.

The invention claimed is:

1. A treatment pad for a dielectric barrier discharge plasma treatment of tissue to be treated of an electrically conducting object, wherein the tissue is used as a counter electrode, and wherein the treatment pad comprises:
   a treatment zone, arranged for at least covering a surface of the tissue to be treated;
   a pattern of one or more active areas, integrated in the treatment zone and arranged for generating a dielectric barrier discharge plasma to a first part of the tissue to be treated, each of the one or more active areas comprising:
      a first electrode to be coupled to a high voltage power source;
      a dielectric formed by a coating or foil of a flexible material so that the dielectric shields the first electrode from the surface of the tissue to be treated; and
      a spacer comprising a structured surface of protrusions adjacent a side of the dielectric facing a first part of the surface of the tissue to be treated,
   wherein a complementary pattern of non-active areas is arranged, in the treatment zone, to cover a second part of the surface of the tissue to be treated that is complementary to the first part, and
   wherein the one or more active areas are arranged, in a condition when the treatment pad is reapplied on the object with an offset, to cover the second part of the surface of the tissue to be treated.

2. The treatment pad according to claim 1, wherein the pattern of one or more active areas and the complementary pattern of non-active areas form an alternating pattern of active areas and non-active areas.

3. The treatment pad according to claim 2, wherein the pattern of one or more active areas and complementary pattern of non-active areas comprises one or more elongate active areas and an equal number of non-active areas, wherein the active areas have a long side oriented along a lateral direction and a short side oriented along a horizontal direction, and wherein the active areas and non-active areas are arranged serially along the horizontal direction.

4. The treatment pad according to claim 1, wherein the pattern of one or more active areas and complementary pattern of non-active areas comprises one or more elongate active areas and an equal number of non-active areas, wherein the active areas have a long side oriented along a lateral direction and a short side oriented along a horizontal direction, and wherein the active areas and non-active areas are arranged serially along the horizontal direction.

5. The treatment pad according to claim 1, wherein two or more elongate active areas are equal in size.

6. The treatment pad according claim 1, wherein the offset is a rotation in plane of the treatment zone of one hundred and eighty degrees.

7. The treatment pad according to claim 1, further comprising a set of reference markers, wherein each reference marker is arranged for marking a position on a side of the surface of the tissue to be treated.

8. The treatment pad according to claim 7, wherein the treatment pad comprises flaps symmetrically extending outward from the treatment zone to engage with the set of reference markers.

9. The treatment pad according claim 7, further comprising a pad sticker having an adhesive material to attach the treatment pad to the object.

10. The treatment pad according to claim 9, wherein an outer contour of the pad sticker at least exposes the set of reference markers.

11. The treatment pad according claim 1, further comprising an edge around a circumference of the treatment zone.

12. The treatment pad according claim 1, wherein the distance between adjacent active areas is at least ten millimeters.

13. The treatment pad according claim 1, wherein the treatment zone is arranged for covering a tissue to be treated that is larger than one thousand two hundred millimeter squared.

14. A control unit for controlling a treatment pad for a dielectric barrier discharge plasma treatment of tissue to be treated of an electrically conducting object, wherein the tissue is used as a counter electrode,
   wherein the treatment pad comprises:
      a treatment zone arranged for at least covering a surface of the tissue to be treated;
      a pattern of one or more active areas, integrated in the treatment zone and arranged for generating a dielectric barrier discharge plasma to a first part of the tissue to be treated, each of the one or more active areas comprising:
         a first electrode to be coupled to a high voltage power source;
         a dielectric formed by a coating or foil of a flexible material so that the dielectric shields the first electrode from the surface of the tissue to be treated; and
         a spacer comprising a structured surface of protrusions adjacent a side of the dielectric facing a first part of the surface of the tissue to be treated,
      wherein a complementary pattern of non-active areas is arranged, in the treatment zone, to cover a second part of the surface of the tissue to be treated that is complementary to the first part, and
      wherein the one or more active areas are arranged, in a condition when the treatment pad is reapplied on the object with an offset, to cover the second part of the surface of the tissue to be treated; and
   wherein the control unit comprises:
      a controller; and
      a high voltage power source for controlling the voltage to the one or more active areas,
      wherein the controller is arranged for:
         activating a first subset of active areas in the pattern of one or more active areas when the treatment pad is first applied on an object, and
         activating a second subset of active areas in the pattern of one or more active areas such that a complementary part of the tissue to be treated is covered by the subset of active areas when the treatment pad is reapplied on the object with an offset.

15. The control unit according to claim 14, wherein the controller is additionally arranged for sequentially activating active areas.

16. The control unit according to claim 15, wherein the controller is additionally arranged for having the pattern of one or more active areas provide a dielectric barrier plasma to the tissue to be treated with:
- a predefined first duration and intensity when the treatment pad is first applied on the object, and
- a predefined second duration and intensity when the treatment pad is reapplied on the object with an offset.

17. The control unit according to claim 14, wherein the controller is additionally arranged for having the pattern of one or more active areas provide a dielectric barrier plasma to the tissue to be treated with:
- a predefined first duration and intensity when the treatment pad is first applied on the object, and
- a predefined second duration and intensity when the treatment pad is reapplied on the object with an offset.

* * * * *